United States Patent [19]

Kleiner et al.

[11] 4,138,433
[45] Feb. 6, 1979

[54] PROCESS FOR PREPARING 1,2-OXA-PHOSPHOLANES

[75] Inventors: Hans-Jerg Kleiner, Kronberg; Manfred Finke, Fischbach, both of Fed. Rep. of Germany

[73] Assignee: Hoechst Aktiengesellschaft, Frankfurt am Main, Fed. Rep. of Germany

[21] Appl. No.: 837,887

[22] Filed: Sep. 29, 1977

Related U.S. Application Data

[63] Continuation of Ser. No. 699,256, Jun. 24, 1976, abandoned.

[30] Foreign Application Priority Data

Jun. 26, 1975 [DE] Fed. Rep. of Germany ....... 2528420

[51] Int. Cl.² .............................................. C07F 9/15
[52] U.S. Cl. ................................................ 260/545 P
[58] Field of Search ................................... 260/545 P

[56] References Cited

PUBLICATIONS

Chajrullin, et al., "Z. Obsc. Chim.," 37(1967), No. 4, pp. 871-875.
Chajrullin, et al., "Z. Obsc. Chim.," 37(1967), p. 710.
Chajrullin, et al., "Z. Obsc. Chim.," 38(1968), p. 288.
Pudovik, et al., "Z. Obsc. Chim.," 37(1967), No. 2, pp. 455-460.

Primary Examiner—Anton H. Sutto
Attorney, Agent, or Firm—Curtis, Morris & Safford

[57] ABSTRACT

Preparation of 2,5-dioxo-1,2-oxa-phospholanes having general formula (I)

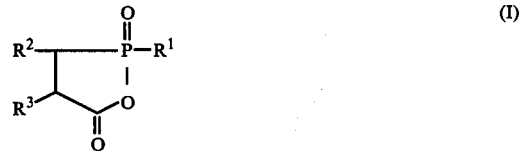

wherein $R^1$ represents an alkyl group being optionally substituted and having up to 18 carbon atoms, a cycloalkyl group having up to 8 carbon atoms, an alkenyl group having up to 8 carbon atoms, an aryl group having up to 14 carbon atoms being possibly substituted by lower alkyl groups, by alkoxy groups, by halogen or by lower alkyl radicals, by alkylated or dialkylated amino groups, or which represents an aralkyl group having up to 15 carbon atoms and being possibly substituted in the same way as the aryl group,
wherein $R^2$ stands for a lower alkyl group or hydrogen and $R^3$ stands for a lower alkyl radical, a phenyl radical being possibly substituted by halogen or lower alkyl groups, for a benzyl radical or for hydrogen.

12 Claims, No Drawings

PROCESS FOR PREPARING 1,2-OXA-PHOSPHOLANES

This is a continuation of application Ser. No. 699,256 filed June 24, 1976, now abandoned.

It is a known fact that 2-chloroformylethyl-phosphinic acid chlorides which are easily accessible from alkyldichlorophosphines and α,β-unsaturated carboxylic acids, may be cyclized with acetanhydride to yield 2,5-dioxo-1,2-oxa-phospholanes, acetylchloride being formed as by-product (V. K. Charjrullin, I. I. Sobcuk and A. N. Pudovik, Z. obsc. Chim. 37, 710 (1967), V. K. Chajrullin, R. M. Kondrat'eva and A. N. Pudovik, Z. obsc. Chim. 38, 288 (1968)):

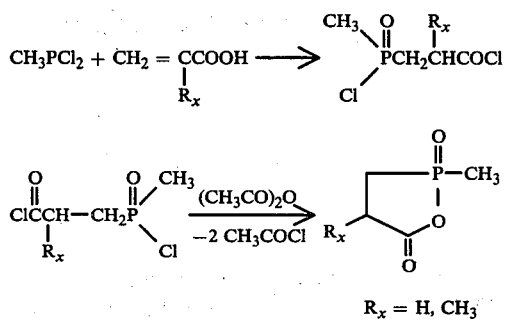

$R_x = H, CH_3$

Publications of the same authors have made known furthermore the cyclization of 2-chloroformethylethylphosphinic acid chlorides by means of 1 mole of ethanol or acetic acid to yield phospholanes.

These processes have the disadvantage that 2-chloroformylethyl-phosphinic acid chlorides have to be prepared in a separate processing step, then purified by distillation and finally, in a second processing step, to be submitted to reaction with the cyclization agent to yield the corresponding phospholanes.

It has now been found that 2,5-dioxo-1,2-oxa-phospholanes having general formula (I)

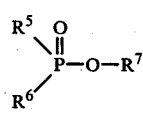

wherein $R^1$ represents an alkyl group, optionally substituted, having up to 18 carbon atoms, preferably from 1 to 12, especially from 1 to 4 carbon atoms, which may carry preferably as three, but especially one substituent halogen, especially chlorine, or a cycloalkyl group having up to 8 carbon atoms, especially cyclohexyl or cyclopentyl, an alkenyl group having up to 8 carbon atoms, especially vinyl or allyl, an aryl group having up to 14 carbon atoms, especially phenyl, which may be substituted — preferably up to twice — by low alkyl groups having up to 4 carbon atoms, lower alkoxy groups having up to 4 carbon atoms, halogen or by amino groups alkylated or dialkylated by lower alkyl radicals having up to 4 carbon atoms, or which represents an aralkyl group being substituted in the same way as the aryl group, and having up to 15 carbon atoms, especially benzyl, wherein $R^2$ stands for an alkyl group having up to 4 carbon atoms, preferably methyl, or hydrogen and wherein $R^3$ stands for an alkyl radical having up to 4 carbon atoms, especially methyl, a phenyl radical which may be substituted up to three times, preferably once or twice, by halogen, preferably chlorine, or low alkyl groups having up to 4 carbon atoms, preferably methyl, for a benzyl radical or for hydrogen, preferably at least one of the radicals $R^2$, $R^3$ represents a hydrogen atom, may be obtained by reacting dihalogenophosphines of general formula (II)

wherein $R^1$ has the same meaning as in formula (I) and wherein X stands for chlorine or bromine, preferably for chlorine, with an equimolar quantity of an α,β-unsaturated acid of formula (III)

wherein $R^2$ and $R^3$ have the same meaning as in formula (I), and simultaneously, especially as a mixture, with an equivalent quantitiy of a compound having formula (IV)

wherein $R^4$ represents hydrogen or an acyl radical having from 2 to 12, preferably from 2 to 8, especially from 2 to 4 carbon atoms, being possibly substituted by a hydroxy group in γ- or δ-position or being substituted from once to three times by halogen, especially by chlorine, or by a carboxyl group, or wherein $R^4$ represents the radical —CO—COOH, an alkyl-sulfonyl radical, phenyl-sulfonyl radical, phenalkyl-sulfonyl radical or alkylphenyl-sulfonyl radical having up to 12 carbon atoms, preferably up to 8 carbon atoms, or wherein $R^4$ represents a radical of formula (IVa)

wherein $R^5$ represents an alkyl radical having up to 12 carbon atoms, preferably up to 8 carbon atoms, especially up to 4 carbon atoms, being possibly substituted from one to three times, especially once, by halogen, especially by chlorine, a cycloalkyl radical having up to 8 carbon atoms, especially cyclopentyl or cyclohexyl, an alkenyl radical having from 2 to 12, preferably from 2 to 6 carbon atoms, especially vinyl or allyl and wherein $R^6$ has the meaning as specified for $R^5$ or is standing for a carboxylic acid group having from 2 to 4 carbon atoms or for $HO(CH_2)_3$— or for $HO(CH_2)_4$—, or with an equivalent quantity of a compound having formula (V),

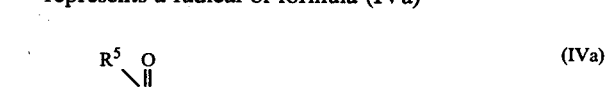

wherein $R^5$ and $R^6$ have the meaning as in formula (IVa) and wherein $R^7$ has the meaning of $R^5$ or represents a group of formula (IVa), or with an equivalent quantity of mixtures of compounds having formulae (IV) and (V) and by isolating the reaction products.

By equivalent quantities, calculated on 1 mole of the starting components having formulae (II) or (III) are to be understood the quotients of molecular weight of the compounds having formulae (IV) or (V), n representing the number of functional groups in the molecule of the compounds having formulae (IV) or (V). Functional groups in respect to the present invention may be: carboxyl groups, sulfonic acid groups, phosphinic acid groups, phosphinic acid ester groups and phosphinic acid anhydride groups.

The process according to the invention yields not only the desired 2,5-dioxo-1,2-oxa-phospholanes depending on the nature of the initial materials of formulae (IV) or (V), but also the reaction product from these latter. Thus there are obtained, besides phospholanes, for example acyl halides, sulfonyl halides, and phosphinic acid halides, which may be isolated and obtained in their pure state. Moreover, in the case of compounds suitable for cyclization such as 3- or 4-hydroxy-alkane carboxylic acid lactones and in the case of 3- or 4-hydroxy-alkylphosphonic acids or their esters phostones are formed which may also be separated and obtained in their pure state. By doubling the employed quantity of compounds having formulae (IV) or (V) it is possible in some cases, of course, to obtain still further products, i.e. in the case of succinic acid or glutaric acid their inner anhydrides, in the case of phosphinic acids or phosphinic acid esters the corresponding phosphinic acid anhydrides.

The following reaction schemes as per the invention may explain more clearly the reactions of dihalogenophosphines with α, β-unsaturated carboxylic acids and compounds having formulae (IV) or (V):

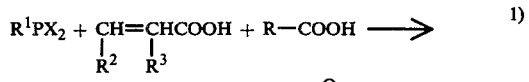

1)

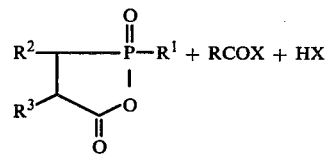

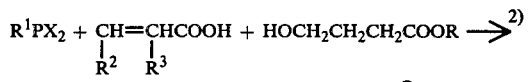

2)

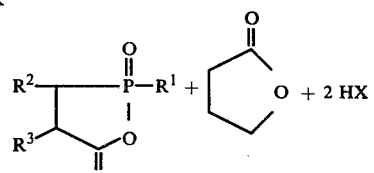

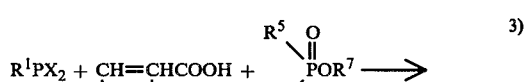

3)

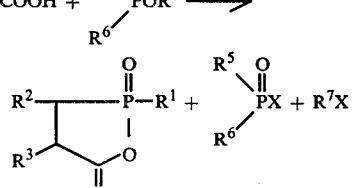

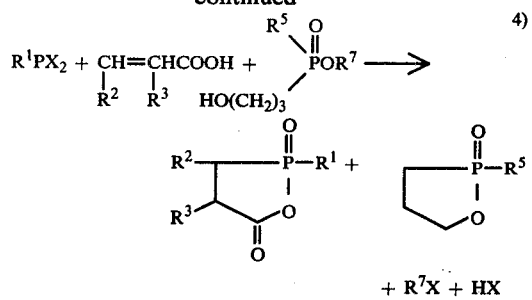

4)

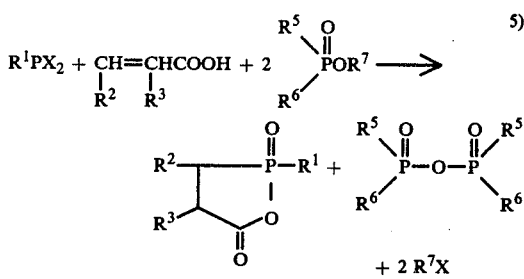

5)

Surprisingly, the dihalogenophosphines can be reacted with a mixture of a α,β-unsaturated carboxylic acid and a compound of formula (IV) or (V) in a reaction without isolation of intermediate products to yield 2,5-dioxo-1,2-oxa-phospholanes, though dihalogenophosphines also react in the absence of α,β-unsaturated carboxylic acids, with compounds of formulae (IV) or (V) to form products which do not paticipate in any reaction with α,β-unsaturated carboxylic acids under the reaction conditions of the process according to the invention. Thus, carboxylic acids such a acetic acid, propionic acid and butyric acid react, even at a temperature below room temperature with alkyl dichlorophosphine to yield 1-hydroxy-alkane-1,1-bis-alkyl-phosphinic acids (German Offenlegungsschrift 2.153.998), which do not cyclize with α,β-unsaturated carboxylic acids to yield 2,5-dioxo-1,2-oxa-phospholanes.

The reactions according to the invention as illustrated by the above equations 1 to 5 may be performed, of course, in two processing steps as well, namely first the addition of α,β-unsaturated carboxylic acid and subsequently the cyclization in the same reaction vessel.

It is to be considered a special advantage of the process according to the invention, that the so-called "one-vessel-reaction" (= reaction without isolation of intermediate products) does away with cumbersome processing steps such as isolation and purification of an intermediate product so that the overall reaction period may be cut down substantially. Moreover, the above-mentioned halides anhydrides and derivatives of phosphinic acid can be prepared by choosing a suitable compound of formulae (IV) or (V) and using a stoichiometric ratio of these compounds to the molar number of the two other reactants.

Suitable dihalogenophosphines of the formula (II) that may be prepared according to known methods and utilized according to the invention are, for example:

Methyldichloro-phosphine, ethyldichloro-phosphine, propyldichloro-phosphine, butyldichloro-phosphine, dodecyldichloro-phosphine, chloromethyldichloro-phosphine, vinyldichloro-phosphine, cyclohexyldichloro-phosphine, benzyldichloro-phosphine, phenyldichloro-phosphine, p-chlorophenyldichloro-phosphine and the corresponding dibromo-phosphines.

Suitable α,β-unsaturated carboxylic acids of formula (III) to be employed are for example acrylic acid, methacrylic acid, crotonic acid, 1-ethyl-acrylic acid, 1-phenyl-acrylic acid.

As suitable compounds of formulae (IV) or (V) may be considered for example:

Acetic acid, propionic acid, butyric acid, caproic acid, monochloro-acetic acid, trifluoro-acetic acid, oxalic acid, malonic acid, succinic acid, glutaric acid, γ-hydroxy-butyric acid, methane-sulfonic acid, ethane-sulfonic acid, propane-sulfonic acid, benzene-sulfonic acid, dimethyl-phosphinic acid, ethylmethyl-phosphinic acid, diethyl-phosphinic acid, methyl-propyl-phosphinic acid, methyl-propyl-phosphinic acid, methyl-dodecylphosphinic acid, diphenyl-phosphinic acid, dimethyl-phosphinic acid-ethyl ester, dimethyl-phosphinic acid-2-chloroethyl ester, methyl-ethyl-phosphinic acid isobutyl ester, methyl-hexyl-phosphinic acid-butyl ester, hydroxymethyl-methyl-phosphinic acid, 3-hydroxypropyl-methylphosphinic acid, dimethyl-phosphinic acid-anhydride, methyl-ethyl-phosphinic acid-anhydride, methyl-butyl-phosphinic acid-anhydride, methyl-phenyl-phosphinic acid-anhydride, diphenyl-phosphinic acid-anhydride.

Preferred compounds are acetic acid, propionic acid, sulfonic acids, dimethyl-phosphinic acid, methyl-ethyl-phosphinic acid and methyl-ethyl-phosphinic acid-isobutyl ester.

Generally, the process according to the invention is carried out in such a way that a mixture of an α,β-unsaturated carboxylic acid and of a compound of formulae (IV) or (V) is added dropwise to the dihalogenophosphines. However, it is also possible to add the dihalogenophosphines to a mixture of the two other reactants. The dihalogenophosphines and the α,β-unsaturated carboxylic acids are utilized in equimolar quantities, whilst the stoichiometric ratio of the compounds of formulae (IV) or (V) to the other reactants depends on whether e.g. halides or - especially in the case of bifunctional compounds - lactones, carboxylic acid-anhydrides or phosphinic acid-anhydrides are desirable by-products. Accordingly, the molar ratio of dihalogenophosphines or α,β-unsaturated carboxylic acids to the monofunctional compounds of formulae (IV) and (V) may therefore be either 1:1 or 1:2, whereas the bifunctional compounds of formulae (IV) and (V) may be employed at a molar ratio of 1:1 or 0.5:1 to the other reactants.

As solubilizers or as diluents there may be added to the dihalogenophosphines or to the two other reactants inert solvents, for example aliphatic, cycloaliphatic, aromatic or araraliphatic hydrocarbons such as xylene, chlorobenzene, toluene, chlorotoluene, dichlorobenzene, benzene fractions boiling at a higher temperature, carbon chlorides such as methylene chloride, chloroform, 1,2-dichloroethane, 1,2-dichloropropane, ethers such as tetrahydrofurane, dioxane, isopropyl ether, di-n-butyl ether, dimethoxy ethane, polyethylene-glycol-dialkyl ether and polypropylene glycol-dialkyl ether. However, it is preferable to carry out the process of the invention in the absence of inert solvents.

The reaction temperature ought to be approximately from −20° C. to +160° C., preferably from 0° C. to +100° C., especially from +15° C. to +80° C. There is no need to keep the reaction temperature at a constant level by exterior cooling devices. When operating without a solvent it may be rather advantageous to allow the reaction temperature to climb to the melting point of the phospholane so as to reduce the viscosity of the reaction mixture.

The reaction time varies generally from about 2 to 6 hours. The reaction mixture is subsequently stirred for approximately half an hour at a temperature of from 100° to 130° C. under normal pressure and furthermore stirred for half an hour at about 130° to 200° C. under water jet vacuum.

The 2,5-dioxo-1,2-oxa-phospholanes may generally be easily separated from the other reaction products by fractional distillation. Highly volatile reaction products can be eliminated while stirring the reaction mixture under normal pressure or under water jet vacuum. It is also possible, however, to separate and purify the reaction mixture by extraction with inert solvents or by recrystallization.

The yields of 2,5-dioxo-1,2-oxa-phospholanes obtained represent about 70–80% of the theoretical yield, calculated on the dihalogenophosphines of formula (II) employed. 2,5-dioxo-1,2-oxa-phospholanes are good flame-retardants which may be utilized for preparing barely flammable, linear polyesters. They represent furthermore valuable intermediate products which may be further processed e.g. to yield flameproofing agents.

The following Examples illustrate the invention:

EXAMPLE 1

2-methyl-2,5-dioxo-1,2-oxa-phospholane based on methyldichlorophosphine, acrylic acid and water A mixture of 225 g (3.12 mole) of acrylic acid and 56 g (3.12 mole) of water is added dropwise at 20°–25° C. to a solution of 365 g (3.12 mole) of methyldichlorophosphine in 600 ml of methylene chloride. During this operation a strong current of hydrogen chloride is discharged. The solvent is distilled off and the reaction mixture subsequently heated under water jet vacuum for about 4 hours to 130°–150° C. After distillation in a film evaporator (boiling point at 1 mm Hg: 164°–170° C.) 322 g of 2-methyl-2,5-dioxo-1,2-oxa-phospolane are obtained, representing a yield of 77% of the theoretical yield, calculated on methyldichlorophosphine.

EXAMPLE 2

2-methyl-2,5-dioxo-1,2-oxa-phospholane based on methyldichlorophosphine, acrylic acid and acetic acid A mixture of 72 g (1 mole) of acrylic acid and 60 g (1 mole) of glacial acetic acid is added dropwise at 25°–30° C. to 117 g (1 mole) of methyl-dichlorophosphine. After termination of the dropwise addition, the reaction solution is heated to 60°–100° C., while acetyl chloride (57 g) is distilled off and a strong current of hydrogen chloride is discharged. In order to eliminate the residual quantities of hydrogen chloride, the reaction mixture is heated under water jet vacuum to an internal temperature of 150° C. The crude phospholane is purified by high vacuum distillation. 98 g of 2-methyl-2,5-dioxo-1,2-oxa-phospholane (boiling point$_{1.5}$: 169° C.) are obtained, representing a yield of 73% of the theoretical yield.

EXAMPLE 3

2-methyl-2,5-dioxo-1,2-oxa-phospholane based on methyldichlorophosphine, acrylic acid and propionic acid A mixture of 36 g (0.5 mole) of acrylic acid and 37 g (0.5 mole) of propionic acid is added dropwise at 20°–30° C. to 58.5 g (0.5 mole) of methyldichlorophosphine. After termination of the dropwise addition the reaction solution is heated to 80°–130° C., while propionic acid chloride (36 g) is distilled off and hydrogen chloride discharged. Subsequently heating takes place under water jet vacuum to 150°–160° C. so as to eliminate the residual quantities of hydrogen chloride. After high vacuum distillation of the crude phospholane 47 g of 2-methyl-2,5-dioxo-1,2-oxa-phospholane (boiling point at 0.7 mm Hg: 160°–162° C.) are obtained, corresponding to a yield of 70% of the theoretical yield.

EXAMPLE 4

2-methyl-2,5-dioxo-1,2-oxa-phospholane based on methyldichlorophosphine, acrylic acid and propane-sulfonic acid A mixture of 36 g (0.5 mole) of acrylic acid and 62 g (0.5 mole) of propane-sulfonic acid is added dropwise to 58.5 g (0.5 mole) of methyldichlorophosphine at 20°–30° C. After termination of the dropwise addition, the temperature is slowly increased to 100° C., while hydrogen chloride is discharged. Subsequently, propane-sulfonic acid chloride (18 g) of distilled off under water jet vacuum at an internal temperature of from 120°–160° C. The high vacuum distillation of the residue yields 51 g of 2-methyl-2,5-dioxo-1,2-oxa-phospholane (boiling point at 2 mm Hg: 185°–190° C.), representing a yield of 76.4% of the theoretical yield.

EXAMPLE 5

2-methyl-2,5-dioxo-1,2-oxa-phospholane based on methyldichlorophosphine, acrylic acid and methyl-ethyl-phosphinic acid A mixture of 36 g (0.5 mole) of acrylic acid and 54 g (0.5 mole) of methyl-ethyl-phosphinic acid is added dropwise at 20°–30° C. to 58.5 g (0.5 mole) of methyldichlorophosphine. After termination of the dropwise addition, the temperature is slowly increased to 100°–120° C., while hydrogen chloride is discharged. Subsequently 40 g of methyl-ethyl-phosphinic acid-chloride are distilled off under water jet vacuum at an internal temperature of 130°–170° C. The high vacuum distillation of the residue yields 47 g of 2-methyl-2,5-dioxo-1,2-oxa-phospholane (boiling point at 1.3 mm Hg: 165°–168° C.), corresponding to a yield of 70% of the theoretical yield.

EXAMPLE 6

2-methyl-2,5-dioxo-1,2-oxa-phospholane based on methyldichlorophosphine, acrylic acid and methyl-ethyl-phosphinic acid-anhydride A mixture of 36 g (0.5 mole) of acrylic acid and 99 g (0.5 mole) of methyl-ethyl-phosphinic acid-anhydride is added dropwise to 58.5 g (0.5 mole) of methyldichlorophosphine at 20°–40° C. After termination of the dropwise addition stirring takes place for 15 minutes at 80°–100° C. Subsequently, 98 g of methyl-ethyl-phosphinic acid-chloride are distilled off under water jet vacuum at an internal temperature of 120°–160° C. The high vacuum distillation of the residue yields 49 g of 2-methyl-2,5-dioxo-1,2-oxa-phospholane, corresponding to a yield of 73% of the theoretical yield.

EXAMPLE 7

2-methyl-2,5-dioxo-1,2-oxa-phospholane based on methyldichlorophosphine, acrylic acid and methyl-ethyl-phosphinic acid-isobutyl ester A mixture of 36 g (0.5 mole) of acrylic acid and 76 g (0.5 mole) of methyl-ethyl-phosphinic acid-isobutyl ester is added dropwise to 58.5 g (0.5 mole) of methyldichloro-phosphine at 25°–50° C. After termination of the dropwise addition approximately 30 g of isobutyl chloride are distilled off under normal pressure. Subsequently, methyl-ethyl-phosphinic acid-chloride (about 26 g) is distilled off under water jet vacuum up to an internal temperature of from 150°–170° C. The residue is submitted to a high vacuum distillation. 51 g of 2-methyl-2,5-dioxo-1,2-oxa-phospholane (boiling point at 0.6 mm Hg: 158° C.) are obtained, corresponding to 76.4% of the theoretical yield.

EXAMPLE 8

2,4-dimethyl-2,5-dioxo-1,2-oxa-phospholane based on methyldichloro-phosphine methacrylic acid and 3-hydroxypropyl-methyl-phosphinic acid A mixture of 43 g (0.5 mole) of methacrylic acid and 69 g (0.5 mole) of 3-hydroxypropyl-methyl-phosphinic acid is added to 58.5 g (0.5 mole) of methyldichlorophosphine at 50°–60° C., while hydrogen chloride is discharged. Subsequently heating takes place under water jet vacuum to an internal temperature of up to 150° C. The residue is distilled under reduced pressure. 35 g of 2-methyl-2-oxo-1,2-oxa-phospholane (boiling point at 1.5 mm Hg: 120°–130° C.) and 55 g of 2,4-dimethyl-2,5-dioxo-1,2-oxa-phospholane (boiling point at 0.7 mm Hg: 150°–155° C.) are obtained. The yield in 2,4-dimethyl-2,5-dioxo-1,2-oxa-phospholane represents 71% of the theoretical yield.

EXAMPLE 9

2-methyl-2,5-dioxo-1,2-oxa-phospholane based on methyldichloro-phosphine acrylic acid and 3-hydroxybutyric acid A mixture of 52 g (0.5 mole) of 3-hydroxy-butyric acid and 36 g (0.5 mole) of acrylic acid is added dropwise to 58.5 g (0.5 mole) of methyl-dichloro-phosphine at 25°–30° C., while hydrogen chloride is discharged. Subsequently 65 g of butyrolactone are distilled off under water jet vacuum up to an internal temperature of 180° C.

The residue is submitted to a vacuum distillation. At a boiling point at 0.7 mm Hg: 173°–175° C. distillation yields 53 g of 2-methyl-2,5-dioxo-1,2-oxa-phospholane, corresponding to a yield of 79% of the theoretical yield.

What is claimed is:

1. Process for preparing 2,5-dioxo-1,2-oxa-phospholanes having general formula (I)

wherein R¹ represents an alkyl group or a substituted alkyl group having up to 18 carbon atoms, a cycloalkyl group having up to 8 carbon atoms, an alkenyl group having up to 8 carbon atoms, an aryl group having up to 14 carbon atoms, which may be substituted by lower alkyl groups having up to 4 carbon atoms, by lower alkoxy groups having up to 4 carbon atoms, halogen or by amino groups alkylated or dialkylated by lower alkyl radicals having up to 4 carbon atoms, or an aralkyl group having up to 15 carbon atoms and which may be substituted in the same way as the aryl group, wherein R² stands for an alkyl group having up to 4 carbon atoms, or hydrogen and wherein R³ stands for an alkyl radical having up to 4 carbon atoms, a phenyl radical or a phenyl radical being substituted by halogen or by lower alkyl groups having up to 4 carbon atoms, for a benzyl radical or hydrogen, which comprises reacting dihalogenophosphines of general formula (II)

  (II)

wherein R¹ has the same meaning as in formula (I) and wherein X stands for chlorine or bromine, with an equimolar quantity of an α,β-unsaturated acid of formula (III)

$$\begin{array}{c} CH=CH-COOH \\ | \quad\quad | \\ R^2 \quad R^3 \end{array}$$ (III)

wherein R² and R³ have the same meaning as in formula (I), and simultaneously, with an equivalent quantity of a compound of formula (IV),

R⁴ — OH     (IV)

wherein R⁴ represents hydrogen or an acyl radical substituted by a hydroxy group in α- or β-position or which may be substituted once, twice or three times by halogen, or by a carboxyl group, or wherein R⁴ represents the radical —CO—COOH, an alkyl-sulfonyl radical, a phenyl-sulfonyl radical, a phenalkyl-sulfonyl radical or an alkylphenyl-sulfonyl radical having up to 12 carbon atoms, or wherein R⁴ represents a radical of formula (IVa),

  (IVa)

wherein R⁵ represents an alkyl radical having up to 12 carbon atoms which may be substituted by halogen, a cycloalkyl radical having up to 8 carbon atoms or an alkenyl radical having from 2 to 12 carbon atoms, and wherein R⁶ has the same meaning as specified for R⁵ or stands for a carboxylic acid group having from 2 to 4 carbon atoms or HO(CH₂)₃— or HO(CH₂)₄—, or with an equivalent quantity of a compound having formula (V)

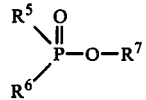  (V)

wherein R⁵ and R⁶ have the same meaning as in formula (IVa) and wherein R⁷ has the meaning of R⁵ or represents a group of formula (IVa), or with an equivalent quantity of mixtures of the compounds having formulae (IV) and (V) and isolating the reaction products.

2. Process according to claim 1, wherein at least one of the radicals R², R³ represents a hydrogen atom.

3. Process according to claim 1, wherein R¹ represents an alkyl group having from 1 to 4 carbon atoms or a halogen-substituted alkyl group having from 1 to 4 carbon atoms, cyclohexyl, cyclopentyl, vinyl, allyl, phenyl or phenyl substituted by lower alkyl groups having up to 4 carbon atoms, lower alkoxy groups having up to 4 carbon atoms, halogen or amine groups alkylated or dialkylated by lower alkyl radicals having up to 4 carbon atoms, or represents benzyl.

4. Process according to claim 1, wherein R² represents methyl.

5. Process according to claim 1, wherein R³ represents methyl.

6. Process according to claim 1, wherein one of the radicals R², R³ represents hydrogen, whilst the other radical represents hydrogen or methyl.

7. Process according to claim 1, wherein the reaction temperature ranges from −20° to +160° C.

8. Process according to claim 1, wherein the reaction temperature ranges from 0° to +100° C.

9. A process for preparing a 2,5-dioxo-1,2-oxa-phospholane having the general formula (I)

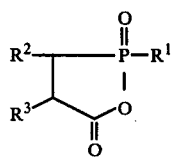  (I)

wherein R¹ represents an alkyl group or a substituted alkyl group having up to 18 carbon atoms, a cycloalkyl group having up to 8 carbon atoms, an alkenyl group having up to 8 carbon atoms, an aryl group having up to 14 carbon atoms, which may be substituted by lower alkyl groups having up to 4 carbon atoms, by lower alkoxy groups having up to 4 carbon atoms, halogen or by amino groups alkylated or dialkylated by lower alkyl radicals having up to 4 carbon atoms, or an aralkyl group having up to 15 carbon atoms and which may be substituted in the same way as the aryl group, wherein R² stands for an alkyl group having up to 4 carbon atoms, or hydrogen and R³ stands for an alkyl radical having up to 4 carbon atoms, a phenyl radical or a phenyl radical substituted by halogen or by lower alkyl groups having up to 4 carbon atoms, or a benzyl radical or hydrogen, which comprises reacting dihalogenophosphines of general formula (II)

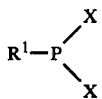

(II)

wherein $R^1$ has the same meaning as in formula (I) and wherein X stands for chlorine or bromine, with an equimolar quantity of an α,β-unsaturated acid of formula (III)

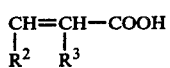

(III)

wherein $R^2$ and $R^3$ have the same meaning as in formula (I), and simultaneously with an equivalent quantity of a carboxylic acid of the formula (IV), $$R^4 — OH \qquad (IV)$$

wherein $R^4$ represents an acyl radical substituted by hydroxy, halogen or carboxy.

10. A process according to claim 9 wherein $R^1$ is methyl, X is chlorine, $R^2$ and $R^3$ are hydrogen and $R^4OH$ is acetic acid.

11. A process according to claim 9 wherein $R^1$ is methyl, X is chlorine, $R^2$ and $R^3$ are hydrogen and $R^4OH$ is propionic acid.

12. A process according to claim 9 wherein $R^1$ is methyl, X is chlorine, $R^2$ and $R^3$ are hydrogen and $R^4OH$ is hydroxybutyric acid.

* * * * *